(12) United States Patent
Maurer et al.

(10) Patent No.: US 8,227,516 B2
(45) Date of Patent: Jul. 24, 2012

(54) COMPOUNDS AS HISTONE DEACETYLASE INHIBITORS

(75) Inventors: Alexander B. Maurer, Bad Homburg (DE); Sascha Hoevelmann, Frankfurt am Main (DE); Elke Martin, Karlsruhe (DE); Bernd Hentsch, Duisburg (DE); Michael Gassen, Munich (DE); Juergen Kraus, Starnberg (DE); Rolf Krauss, Planegg-Martinsried (DE); Adam-Spencer Vincek, Gainesville, FL (US)

(73) Assignee: 4SC Discovery GmbH, Planegg-Martinsried (DE)

( * ) Notice: Subject to any disclaimer, the term of this patent is extended or adjusted under 35 U.S.C. 154(b) by 1294 days.

(21) Appl. No.: 11/778,297

(22) Filed: Jul. 16, 2007

(65) Prior Publication Data

US 2009/0088478 A1   Apr. 2, 2009

Related U.S. Application Data

(62) Division of application No. 10/624,571, filed on Jul. 23, 2003, now abandoned.

(60) Provisional application No. 60/397,663, filed on Jul. 23, 2002.

(51) Int. Cl.
*A61K 31/16* (2006.01)

(52) U.S. Cl. ........................................ 514/627; 514/629

(58) Field of Classification Search ........................ None
See application file for complete search history.

(56) References Cited

U.S. PATENT DOCUMENTS

| 5,712,300 A | 1/1998 | Jacobsen |
| 6,897,220 B2 | 5/2005 | Delorme et al. |

FOREIGN PATENT DOCUMENTS

| EP | 0 200 377 | 12/1986 |
| WO | WO98/52910 | 11/1998 |

OTHER PUBLICATIONS

Stowell et al., Synthesis of N-Hydroxy-N-phenyloctanediamine and its inhibitory Effect on Proliferation of AXC rar Prostate Cancer! Cells, Journal of Medicinal Chemistry 1995, vol. 38, pp. 1141-1413.

*Primary Examiner* — James D Anderson
(74) *Attorney, Agent, or Firm* — Baker, Donelson, Bearman, Caldwell & Berkowitz, PC

(57) ABSTRACT

The present invention relates to compounds as inhibitors of enzymes having histone deacetylase activity, to the processes for the preparation of those compounds, and to their use for the treatment of diseases which are associated with hypoacetylation of histones and/or other molecules, or in which induction of hyperacetylation has a beneficial effect for example by inhibition of proliferation and/or induction of differentiation and/or induction of apoptosis in transformed cells, such as cancer. Furthermore, the compounds are useful for the treatment of other proliferative diseases, for therapy or prophylaxis of conditions associated with abnormal gene expression.

5 Claims, 7 Drawing Sheets

Figure 6

| CELL LINE | COMPOUND 1 [µM] | COMPOUND 2 [µM] | COMPOUND 3 [µM] |
|---|---|---|---|
| MCF-7 (breast) | 25 | 15 | 2.5 |
| ZR-75-30 (breast) | 15 | 9,5 | 2.3 |
| Colo320 (colon) | 8 | 5 | 0.53 |
| HT-29 (colon) | 65 | 23 | 2.5 |
| HCT-15 (colon) | 63 | 26 | 2.8 |
| LoVo (colon) | 19 | 17 | 0.9 |
| Capan 1 (pancreas) | 70 | 22 | 8 |
| DU-145 (prostate) | 23 | 7 | 2.8 |
| PC3 (prostate) | 11 | 7 | 1.3 |

COMPOUNDS AS HISTONE DEACETYLASE INHIBITORS

CROSS REFERENCE TO RELATED APPLICATIONS

This application is a divisional of U.S. application Ser. No. 10/624,571, filed Jul. 23, 2003, now abandoned which claims priority from Provisional Application Ser. No. 60/397,663, filed Jul. 23, 2002, the content of which is incorporated herein by reference in its entirety.

BACKGROUND OF THE INVENTION

1. Field of the Invention

The present invention relates to compounds as inhibitors of enzymes having histone deacetylase activity, to the processes for the preparation of those compounds, and to their use for the treatment of diseases which are associated with hypoacetylation of histones and/or other molecules, or in which induction of hyperacetylation has a beneficial effect for example by inhibition of proliferation and/or induction of differentiation and/or induction of apoptosis in transformed cells, such as cancer. Furthermore, the compounds are useful for the treatment of other proliferative diseases, for therapy or prophylaxis of conditions associated with abnormal gene expression.

2. Description of the Related Art

Local remodeling of chromatin is a key step in the transcriptional activation of genes. Dynamic changes in the nucleosomal packaging of DNA must occur to allow transcriptional proteins to contact with the DNA template. One of the most important mechanisms influencing chromatin remodeling and gene transcription are the posttranslational modification of histones and other cellular proteins by acetylation and subsequent changes in chromatin structure (Davie, 1998, Curr Opin Genet Dev 8, 173-8; Kouzarides, 1999, Curr Opin Genet Dev 9, 40-8; Strahl and Allis, 2000, Nature 403, 41-4). In the case of histone hyperacetylation, changes in electrostatic attraction for DNA and steric hindrance introduced by the hydrophobic acetyl group leads to destabilisation of the interaction of histones with DNA. As a result, acetylation of histones disrupts nucleosomes and allows the DNA to become accessible to the transcriptional machinery. Removal of the acetyl groups allows the histones to bind more tightly to DNA and to adjacent nucleosomes and thus to maintain a transcriptionally repressed chromatin structure. Acetylation is mediated by a series of enzymes with histone acetyltransferase (HAT) activity. Conversely, acetyl groups are removed by specific histone deacetylase (HDAC) enzymes. Disruption of these mechanisms gives rise to transcriptional misregulation and may lead to tumorigenic transformation.

Additionally, other molecules such as transcription factors alter their activity and stability depending on their acetylation status. E.g. PML-RAR, the fusion protein associated with acute promyelocytic leukemia (APL) inhibits p53 through mediating deacetylation and degradation of p53, thus allowing APL blasts to evade p53 dependent cancer surveillance pathways. Expression of PML-RAR in hematopoietic precursors results in repression of p53 mediated transcriptional activation, and protection from p53-dependent apoptosis triggered by genotoxic stresses (X-rays, oxidative stress). However, the function of p53 is reinstalled in the presence of HDAC inhibitors implicating active recruitment of HDAC to p53 by PML-RAR as the mechanism underlying p53 inhibition (Insinga et al. 2002, manuscript submitted). Therefore, factor acetylation plays a crucial role in the anti-tumor activity of HDAC inhibitors.

Nuclear hormone receptors are ligand-dependent transcription factors that control development and homeostasis through both positive and negative control of gene expression. Defects in these regulatory processes underlie the causes of many diseases and play an important role in the development of cancer. Many nuclear receptors, including T3R, RAR and PPAR, can interact with the corepressors N-CoR and SMRT in the absence of ligand and thereby inhibit transcription. Furthermore, NCoR has also been reported to interact with antagonist-occupied progesterone and estrogen receptors. N-CoR and SMRT have been shown to exist in large protein complexes, which also contain mSin3 proteins and histone deacetylases (Pazin and Kadonaga, 1997; Cell 89, 325-8). Thus, the ligand-induced switch of nuclear receptors from repression to activation reflects the exchange of corepressor and coactivator complexes with antagonistic enzymatic activities.

The N-CoR corepressor complex not only mediates repression by nuclear receptors, but also interacts with additional transcription factors including Mad-1, BCL-6 and ETO. Many of these proteins play key roles in disorders of cell proliferation and differentiation (Pazin and Kadonaga, 1997, Cell 89, 325-8; Huynh and Bardwell, 1998, Oncogene 17, 2473-84; Wang, J. et al., 1998, Proc Natl Acad Sci USA 95, 10860-5). T3R for example was originally identified on the basis of its homology with the viral oncogene v-erbA, which in contrast to the wild type receptor does not bind ligand and functions as a constitutive repressor of transcription. Furthermore, mutations in RARs have been associated with a number of human cancers, particularly acute promyelocytic leukemia (APL) and hepatocellular carcinoma. In APL patients RAR fusion proteins resulting from chromosomal translocations involve either the promyelocytic leukemia protein (PML) or the promyelocytic zinc finger protein (PLZF). Although both fusion proteins can interact with components of the corepressor complex, the addition of retinoic acid dismisses the corepressor complex from PML-RAR, whereas PLZF-RAR interacts constitutively. These findings provide an explanation why PML-RAR APL patients achieve complete remission following retinoic acid treatment whereas PLZF-RAR APL patients respond very poorly (Grignani et al., 1998, Nature 391, 815-8; Guidez et al., 1998, Blood 91, 2634-42; He et al., 1998, Nat Genet 18, 126-35; Lin et al., 1998, Nature 391, 811-4). Furthermore, a PML-RAR patient who had experienced multiple relapses after treatment with retinoic acid has recently been treated with the HDAC inhibitor phenylbutyrate, resulting in complete remission of the leukemia (Warrell et al., 1998, J. Natl. Cancer Inst. 90, 1621-1625).

By now, a clinical phase II trial with the closely related butyric acid derivative Pivanex (Titan Pharmaceuticals) as a monotherapy has been completed demonstrating activity in stage III/IV non-small cell lung cancer (Keer et al., 2002, ASCO, Abstract No. 1253). More HDAC inhibitors have been identified, with NVP-LAQ824 (Novartis) and SAHA (Aton Pharma Inc.) being members of the structural class of hydroxamic acids tested in phase I clinical trials (Marks et al., 2001, Nature Reviews Cancer 1, 194-202). Another class comprises cyclic tetrapeptides, such as depsipeptide (FR901228— Fujisawa) used successfully in a phase II trial for the treatment of T-cell lymphomas (Piekarz et al., 2001, Blood 98, 2865-8). Furthermore, MS-27-275 (Mitsui Pharmaceuticals), a compound related to the class of benzamides, is now being tested in a phase I trial patients with hematological malignancies.

In Int. J. Chem. Kinet. 1997, 29, 729-735 3-Cyclopentyl-N-hydroxy-propionamide, 4-Cyclohexyl-N-hydroxy-butyramide and 2-Cyclohexyl-N-hydroxy-acetamide are described (see also Berndt et al., 1992, Int. J. Chem. Kinet., 24, 695-701).

The crystal structure of a histone deacetylase like protein from the hyperthermophilic bacterium *aquifex aeolicus* cocrystallized with the two inhibitors TSA and SAHA is described by Finnin et al., 1999, Nature, 401, 188-193.

Hydroxamic acids with at least one aromatic ring or ring system as histone deacetylase inhibitors are described by Lavoie et al., 2001, Bioorg. Med. Chem. Letters 11, 2847-2850; Remiszewski et al., 2002, J. Med. Chem. 45, 4, 753-757; Massa et al., 2001, J. Med. Chem. 44, 2069-2072; Sternson et al., 2001, Org. Lett. 3, 26, 4239-4242; Mai et al., 2002, J. Med. Chem. 45, 1778-1784; Woo et al., 2002, J. Med. Chem. 45, 2877-2885.

In EP1174438, WO0052033, WO0118045, WO0118171, WO0138322, WO0170675, WO9735990, WO9911659, WO0226703, WO0230879 and WO0226696 hydroxamic acids as histone deacetylase inhibitors are described.

In WO9805635 and WO9533709 hydroxamic acids as matrix metalloproteinase inhibitors are described.

SUMMARY OF THE INVENTION

The compounds of the present invention are hydroxamic acids which are inhibitors of enzymes having histone deacetylase activity. Due to their HDAC-inhibitory activity they induce differentiation and/or apoptosis in a wide variety of cancer cells for three reasons: (1) these enzymes are present in all cells and (2) pilot studies with model compounds such as butyrate or TSA which are different from those described in this invention had shown that HDAC inhibitors induce differentiation in a wide variety of cells and (3) clinical efficacy has been demonstrated for several other HDAC inhibitors unrelated to the presented compounds in the treatment of cancer patients.

The activity to induce differentiation and/or apoptosis in a wide variety of transformed cells is a much more complex biological activity than only the inhibition of proliferation. In the latter case it would not be evident, why only the proliferation of transformed (tumor) but not of normal cells should be inhibited. The induction of apoptosis, differentiation or more specifically re-differentiation in dedifferentiated tumor cells provides a rationale why the compounds of this invention have beneficial effects in a wide variety of tumors by induction of differentiation and/or apoptosis.

The histone deacetylase inhibitory activity of new compounds may be determined by a number of state-of-the-art technologies such as transcriptional repression assay, Western Blot analysis which detects acetylation of histone H3 and/or histone H4, or by an enzymatic in vitro assay. Histone deacetylase inhibitors can be further characterized for their cytotoxic and growth inhibitory effects on tumor cell lines and for their ability to modulate gene expression patterns in cells.

The present invention is directed to compounds of the general formula (I):

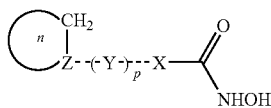

or pharmaceutical acceptable salts or physiologically functional derivatives thereof wherein:

n is a non-aromatic ring system containing two to six carbon atoms, wherein the ring system can contain one ore two double bonds;

X is C, CH or CH2;

Y is selected from C, CH, CH₂, S, NR, CH₂—CH₂, H₂C—
—C H, HC— —CH₂, C—CH₂, H₂C—C, or C— —C;
one or more of the hydrogen atoms can optionally be substituted by one or more substituents R'; each of the dotted lines means a single, a double or triple bond with the exclusion of a combination of a triple bond and a double with a triple bond;

R' is independently H, —CN, alkyl, cycloalkyl, aminoalkyl, alkylamino, alkoxy, —OH, —SH, alkylthio, hydroxyalkyl, hydroxyalkylamino, halogene, haloalkyl, haloalkyloxy;

R is H, an alkyl or cycloalkyl group;

Z is CH, C, or P;

p is 0 or 1; and with the proviso that the following compounds are excluded:

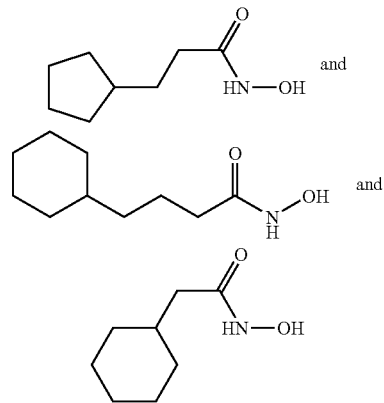

An alkyl group, if not stated otherwise, is preferably a linear or branched chain of 1 to 6 carbon atoms, preferably a methyl, ethyl, propyl, isopropyl, butyl, t-butyl, isobutyl, pentyl or hexyl group, a methyl, ethyl, isopropyl or t-butyl group being most preferred.

The term "alkyl", unless otherwise noted, is also meant to include those derivatives of alkyl defined in more detail below as "unsaturated alkyl". An unsaturated alkyl group is one having one or more double bonds or triple bonds, preferably vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers.

The alkyl group in the compounds of formula (I) can optionally be substituted by one or more substituents R' being as defined above.

An cycloalkyl group denotes a non-aromatic ring system containing 3 to 8 carbon atoms, wherein one or more of the carbon atoms in the ring can be replaced by a group X, X being as defined above.

An alkoxy group denotes an O-alkyl group, the alkyl group being as defined above.

An alkylthio group denotes an S-alkyl group, the alkyl group being as defined above.

A hydroxyalkyl group denotes an HO-alkyl group, the alkyl group being as defined above.

An haloalkyl group denotes an alkyl group which is substituted by one to five preferably three halogen atoms, the alkyl group being as defined above; a $CF_3$ being preferred.

An haloalkyloxy group denotes an alkoxy group which is substituted by one to five preferably three halogen atoms, the alkoxy group being as defined above; a $OCF_3$ being preferred.

A hydroxyalkylamino group denotes an $(HO\text{-alkyl})_2$-N-group or HO-alkyl-NH-group, the alkyl group being as defined above.

An alkylamino group denotes an HN-alkyl or N-dialkyl group, the alkyl group being as defined above.

An aminoalkyl group denotes an $H_2N$-alkyl, monoalkylaminoalkyl, or dialkylaminoalkyl group, the alkyl group being as defined above.

A halogen group is chlorine, bromine, fluorine or iodine, fluorine being preferred.

The invention also provides a pharmaceutical composition comprising a compound of formula (I) in free form or in the form of pharmaceutically acceptable salts and physiologically functional derivatives or prodrugs, together with a pharmaceutically acceptable diluent or carrier therefore.

DETAILED DESCRIPTION OF THE INVENTION

The term "physiologically functional derivative" as used herein refers to compounds like ethers, esters, N-alkylated or acetylated hydroxamic acids, 2,5-dihydro-[1,2,4]-oxodiazolyl or 4,5-dihydro-[1,2,4]-oxodiazolyl, which are not pharmaceutically active themselves but which are transformed into their pharmaceutical active form in vivo, i.e. in the subject to which the compound is administered.

In another aspect, the present invention also provides a method for the treatment or prophylaxis of a condition, where there is an advantage in inhibiting histone deacetylase activity which comprises the administration of an effective amount of a compound of formula (I) and physiologically acceptable salts or physiologically functional derivatives thereof.

The invention is also directed to the use of compounds of the formula (I) and of their pharmacologically tolerable salts or physiologically functional derivatives for the production of a medicament for the prevention and treatment of diseases, where inhibition of histone deacetylase is of benefit.

In addition, the present invention provides methods for preparing the desired hydroxamic acides of the formula (I).

One method for the synthesis of compounds of the formula (I) comprises the conversion of an acid (formula II) to the corresponding acid chloride (formula III) and reacting the acid chloride with hydroxylamine (Watanabe et al., 1989, J. Org. Chem., 54, 17, 4088-4097; Shishido et al., 1992, J. Org. Chem., 57, 10, 2876-2883).

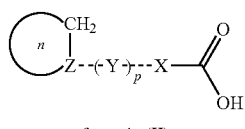

formula (II)

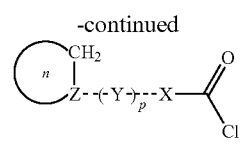

formula (III)

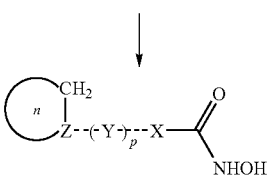

formula (I)

Coupling reactions of acids of the formula (II) with hydroxylamine, other methods for the preparation of compounds of the formula (I), are described by Woo et al., 2002, J. Med. Chem. 45, 2877-2885; Knorr et al., 1989, Tetrahedron Lett., 30, 1927-1930, Carpino, 1993, J. Am. Chem. Soc., 115, 4397-4398 and Albericio et al., 1998, J. Org. Chem., 63, 9678-9683.

Another method for the preparation of compounds of the formula (I) is the reaction of the corresponding ester with hydroxylamine as described by Stowell et al., 1995, J. Med. Chem., 38, 8, 1411-1413.

In one preferred embodiments in the compounds of formula (I) the ring n including Z can be cyclopentyl, cyclohexyl, cycloheptyl, cyclopent-1-enyl, cyclohex-1-enyl, cyclohept-1-enyl, cyclopent-2-enyl, cyclohex-2-enyl, cyclohept-2-enyl, cyclohex-3-enyl, cyclohept-3-enyl.

In another preferred embodiment in the compounds of the formula (I) of the present invention the ring n including Z is cyclopentyl or cyclohexyl, and Y is selected from CH, $CH_2$, $CH_2$—$CH_2$, S, NR or p=0, and Z is CH or P.

In another more preferred embodiment in the compounds of the formula (I) of the present invention the ring n including Z is cyclopentyl or cyclohexyl, Y is selected from CH, $CH_2$, $CH_2$—$CH_2$, or p=0 and Z is CH.

In another more preferred embodiment, none of the carbon atoms of the alkyl groups is replaced by a group A.

Preferred compounds of the present invention are:
3-Cyclopentyl-N-hydroxy-propionamide;
3-Cyclohexyl-N-hydroxy-propionamide;
4-Cyclohexyl-N-hydroxy-butyramide;
2-Cycloheptyl-N-hydroxy-acetamide.

The compounds of the formula (I) according to the invention can form salts with inorganic or organic acids or bases. Examples of such salts are, for example, alkali metal salts, in particular sodium and potassium salts, or ammonium salts.

The compounds of formula (I) may be obtained via various methods. In preferred embodiments of the methods of the invention the two following methods of synthesis are used.

Acids or acid chlorids of α-β unsaturated compounds of the formula (I) can be obtained by hydrolysis of the corresponding ester to result the acid (Bojic et al., 1998, 354, 289-299) which can be converted with chlorinating agents (oxalylchloride, thionylchloride, phosphorpenta chloride) into the acid chloride. α-β unsaturated esters can be synthesized from the corresponding aldehyde by reacting them with Carbethoxymethylene)triphenylphosphorane (PhP=CHCOOEt) (Maryanoff et al., 1989, Chem. Rev. 89, 863-927).

Other methods for preparing different acids are described by Mancuso et al., 1981, Synthesis, 165-185; or Bal et al., 1981, Tetrahedron, 37, 2091-2096.

The compounds of the present invention can be used for a variety of human and animal diseases, preferably human diseases, where inhibition of histone deacetylase activity is beneficial.

Therefore the compounds according to the invention and medicaments prepared therewith are generally useful to induce the differentiation and/or apoptosis of cells such as undifferentiated tumor cells. The therapeutic effect of the invention may arise through one or more mechanisms, including but not limited to, the regulation of cell proliferation, cell activation, cell survival cell differentiation, cell cycle, cell maturation and cell death or to induce systemic changes in metabolism such as changes in sugar, lipid or protein metabolism, the inhibition of new blood vessel formation (antiangiogenesis), the inhibition of tumor spread into other organs (anti-metastatic), the inhibition of tumor spread into neighboring normal structures (anti-invasive) or the promotion of programmed cell death (apoptosis).

They can also be used to support cell generation poiesis, including blood cell growth and generation (prohematopoietic effect) after depletion or destruction of cells, as caused by, for example, toxic agents, radiation, immunotherapy, growth defects, malnutrition, malabsorption, immune dysregulation, anemia and the like or to provide a therapeutic control of tissue generation and degradation, and therapeutic modification of cell and tissue maintenance and blood cell homeostasis.

The compounds according to the invention and medicaments prepared therewith are also useful for the treatment of a disease which is associated with gene-specific hypoacetylation of histones or other molecules, such as p53. Additionally, the compounds of the present invention may also be used in the treatment of conditions where the suppression of anti-apoptotic genes, such as BCL-XL and other BCL family members, or the induction of tumor suppressor activity of molecules such as p21 and/or p53, is required.

The compounds according to the invention and medicaments prepared therewith are also suitable for the treatment of diseases in which the induction of hyperacetylation of histones has a beneficial effect resulting in differentiation and/or apoptosis of a patient's tumor cells and thus causing a clinical improvement of the patient's condition. Examples of such diseases include but are not limited to, skin cancer, melanoma, estrogen receptor-dependent and independent breast cancer, ovarian cancer, testosteron receptor-dependent and independent prostate cancer, renal cancer, colon and colorectal cancer, pancreatic cancer, bladder cancer, esophageal cancer, stomach cancer, genitourinary cancer, gastrointestinal cancer, uterine cancer, astrocytomas, gliomas, basal cancer and squameous cell carcinoma, sarcomas as Kaposi's sarcoma and osteosarcoma, head and neck cancer, small cell and non-small cell lung carcinoma, leukemia, lymphomas and other blood cell cancers, Keratoakantoma, Bowen Disease, cutaneous T-Cell Lymphoma and also for the treatment of pre-malignant lesions (such as Actinic Keratose).

The combinatorial treatment of the present invention is particularly useful for treating minimal residual tumor disease or tumor metastases.

Additionally, the invention may also be beneficial by reverting inappropriate gene expression in diseases based on aberrant recruitment of histone deacetylase activity such as thyroid resistance syndrome, or in other conditions associated with abnormal gene expression, such as inflammatory disorders, diabetes, thalassemia, cirrhosis, protozoal infection, or the like and all types of autoimmune diseases, in particular rheumatoid arthritis, rheumatoid spondylitis, all forms of rheumatism, osteoarthritis, gouty arthritis, multiple sclerosis, insulin dependent diabetes mellitus and non-insulin dependent diabetes, asthma, rhinitis, uveithis, lupus erythematoidis, ulcerative colitis, Morbus Crohn, inflammatory bowel disease, as well as other chronic inflammations, chronic diarrhea and of inflammations of the skin and/or mucosa (such as Psoriasis, Ichtiosis, Acne). The invention also relates to the use for the protection from UV light and for the treatment of sun burn.

Furthermore, the compounds according to the invention and medicaments prepared therewith are useful for the treatment of other proliferative diseases such as psoriasis, fibrosis, warts and other dermatological disorders. The terms "proliferative disease", and "cell proliferation", are used interchangeably herein and relate to an unwanted or uncontrolled cellular proliferation of excessive or abnormal cells which is undesired, such as, neoplastic or hyperplastic growth, whether in vitro or in vivo. Examples of proliferative conditions include, but are not limited to, pre-malignant and malignant cellular proliferation, including malignant neoplasms and tumors, cancers, leukemias, psoriasis, bone disease, fibroproliferative disorders (e.g. of connective tissues), and atherosclerosis. Any type of cell may be treated, including but not limited to, lung, colon, breast, ovarian, prostate, liver, pancreas, brain, and skin and any treatment of disorders involving T-cells such as aplastic anemia and DiGeorge syndrome, Graves' disease.

The invention encompasses also compounds of formula (I) which are metabolized in patients to a compound of the presented formula. The embodiments described in this invention apply to such compounds as well.

The present invention also concerns a diagnostic method to identify tumors comprising the step of testing in vitro whether a tumor is responsive to treatment either with compounds of formula (I) or in combination with established tumor therapeutics. The method preferably comprises the method for the identification of genes regulated by these treatments. In a particular embodiment, the diagnostic method comprises the use of nucleic acid technology, preferably of hybridization or polymerase chain reaction for detection. Other types of nucleic acid technology, however, may be employed. In another embodiment the method comprises the use of specific antibodies against differentially regulated proteins for detection. For this purpose proteins encoded by the genes showing deregulation of their expression upon combinatorial treatment using formulations of this invention and derivatives thereof would be expressed e.g. in recombinant expression systems and antibodies directed against these proteins would be generated. Subsequently such antibodies could be used (or patterns of antibodies) to characterize the status of a tumor or tumor cells for diagnostic and/or prognostic reasons.

In general the present invention provides novel possibilities to treat various human diseases. Applicants found that the HDAC inhibitory and cellular differentiation-inducing activity of compounds of formula (I) can be used successfully in combination with well established and clinically used therapeutic drugs for the treatment of tumor cells of different origins. Such compound based combinatorial treatment is considered to generate superior therapeutic success in human tumor patients than the corresponding therapeutic drugs used on their own. It is an object of the present invention to provide combinatorial therapeutic approaches using the presented compounds for the treatment of cancer. Such combinatorial treatments could result in a decrease of the therapeutic doses of e.g. chemotherapeutic reagents required and could thus limit the currently observed, partly very serious side effects of frequently used therapies.

Aspects of the present invention are the combination of compounds of formula (I) with, but not restricted to, therapeutic principles currently in clinical use or in clinical development, such as Chemotherapeutic or cytotoxic drugs (e.g. 5-FU, taxol, cisPlatinum, camptothecin, gemcitabine, doxorubicine, irinothecan)

differentiation inducing drugs (e.g. vitamin D, retinoic acid, cytokines such as 11-3, 11-6, SCF, G-CSF, GM-CSF, TNF)

Radiation therapy (e.g. x-rays or gamma rays)

immunological approaches (antibody therapy, vaccination)

combined immunotherapeutic/cytotoxic approaches (e.g. antibodies conjugated with cytotoxic components)

anti-angiogenesis approaches.

The compounds and salts thereof can be formulated as pharmaceutical compositions (e.g. liquids, suspensions, emulsions, lozenges, cachets, ampoules, suppositories, pessaries, ointments, gels, pastes, sprays, lotions, oils, boluses, electuaries, aerosols, powders, granules, tablets, pills, capsules, injections, solutions, foams, creams, enemas and the like) comprising at least one such compound alone or in admixture with pharmaceutically acceptable carriers, excipients and/or diluents. The pharmaceutical compositions can be formulated in accordance with a conventional method.

Specific dose levels for any particular patient will be employed depending upon a variety of factors including the age, body weight, general health, sex, diet, and prior medication, and the severity of the particular disease of the patient, and the activity of specific compounds employed, time of administration, route of administration, rate of excretion, the duration of the treatment, other drugs, compounds, and/or materials used in combination. It will be appreciated that the appropriate dosage of the active compounds, and compositions comprising the active compounds, can vary from patient to patient. Determining the optimal dosage will generally involve balancing of the level of therapeutic benefit against any risk or deleterious side effects of the treatments of the present invention.

Administration in vivo can be effected in one dose, continuously or intermittently throughout the course of treatment. Methods of determining the most effective means and dosages of administration are well known to those of skill in the art and will vary with the formulation used for therapy, the purpose of the therapy, the target cell being treated, and the subject being treated. Single or multiple administrations can be carried out with the dose level and pattern being selected by the treating physician.

In general, a suitable dose of the active compound is in the range of about 0.1 to about 500 mg per kilogram body weight preferably 0.1 to 100 mg per kilogram body weight of the subject per day. Where the active ingredient is a salt, an ester, prodrug, or the like, the amount administered is calculated on the basis the parent compound and so the actual weight to be used is increased proportionately.

BRIEF DESCRIPTION OF THE DRAWINGS

FIG. 6 shows the concentration of Compounds 1, 2 and 3 inducing a 50% reduction in cellular biomass ($IC_{50}$) after treatment of various cancer cell lines for 72 hours.

EXAMPLES

Example 1

Figure 1:
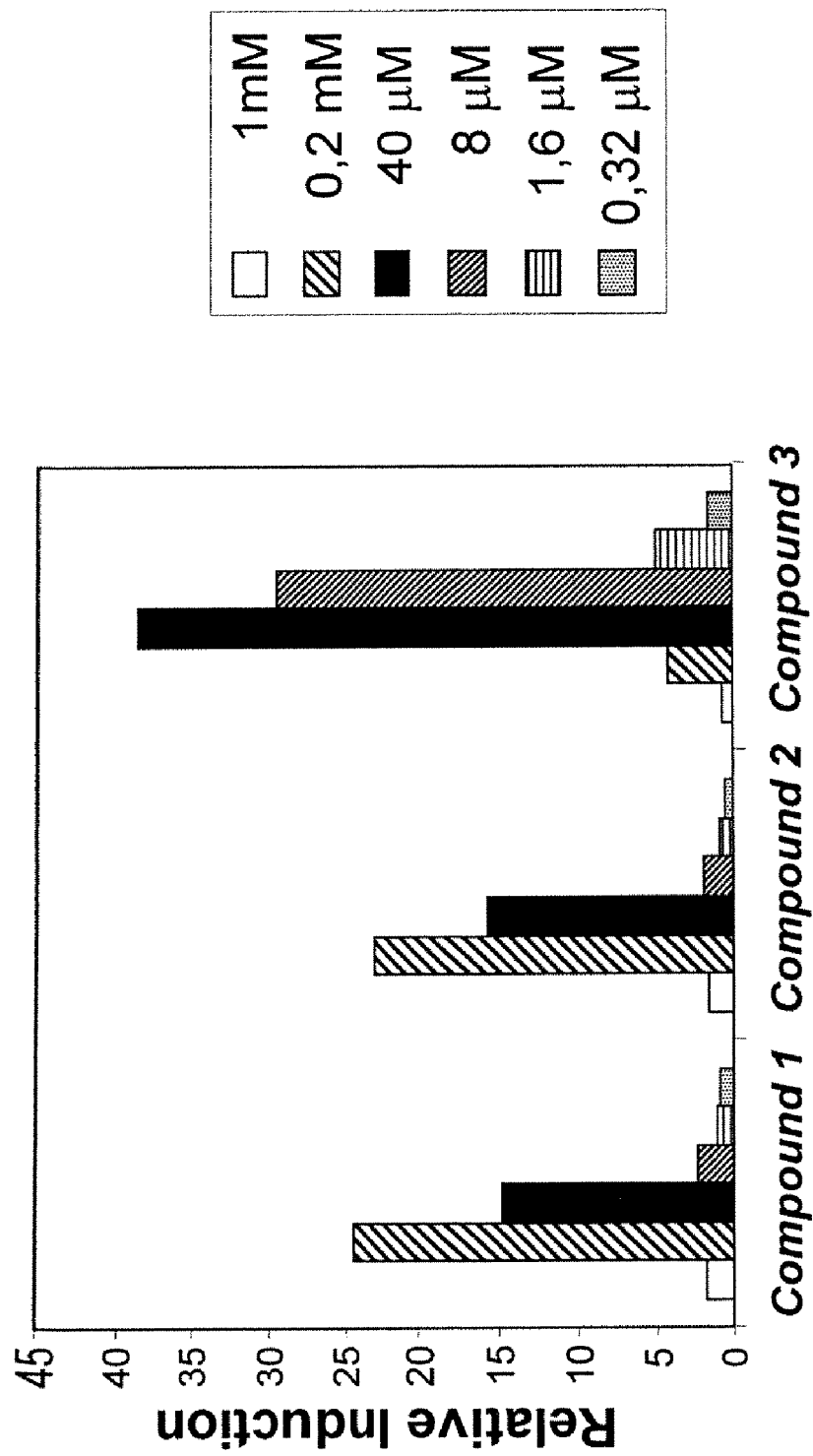
FIG. 1 shows the relief of HDAC-dependent transcriptional repression in a reporter cell line, UAS TK-luc, after 24 hours treatment with Compound 1, 2 and 3. Depicted is the fold induction of luciferase expression after treatment of cells at the indicated concentrations of Compounds 1, 2 and 3.
Figure 2:
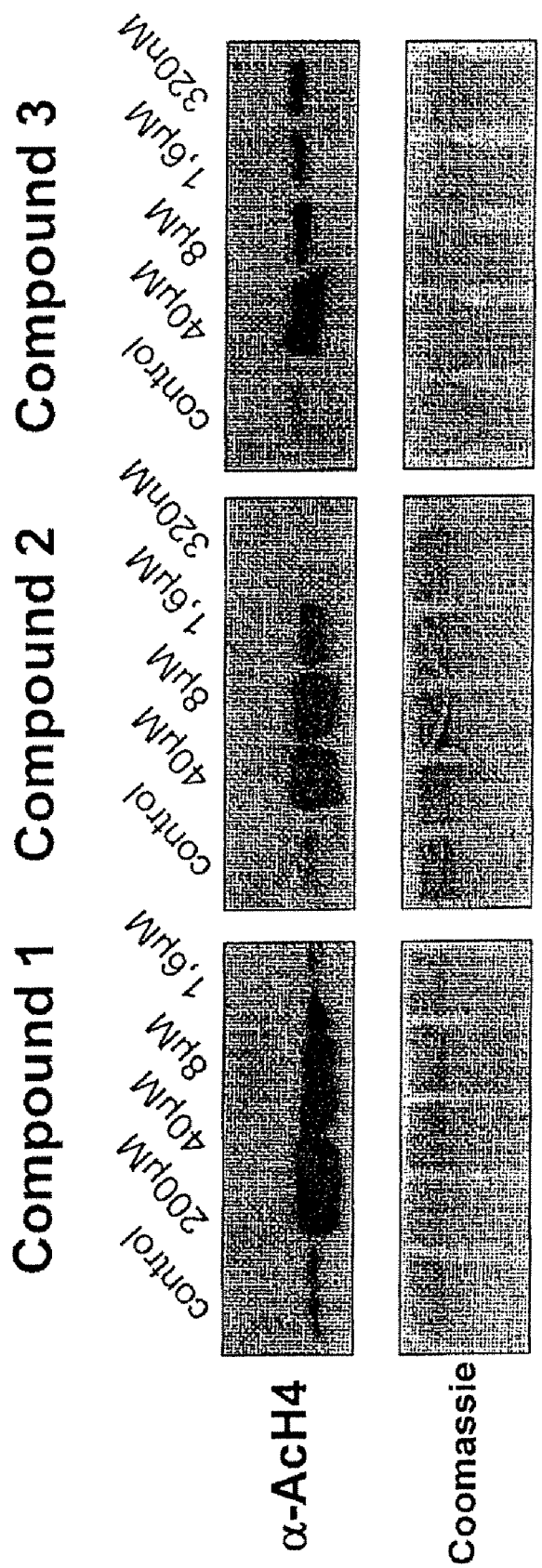
FIG. 2 shows the induction histone H4 hyperacetylation in 293T cells after treatment with Compounds 1, 2 and 3 for six hours at the indicated concentrations.
Figure 3:
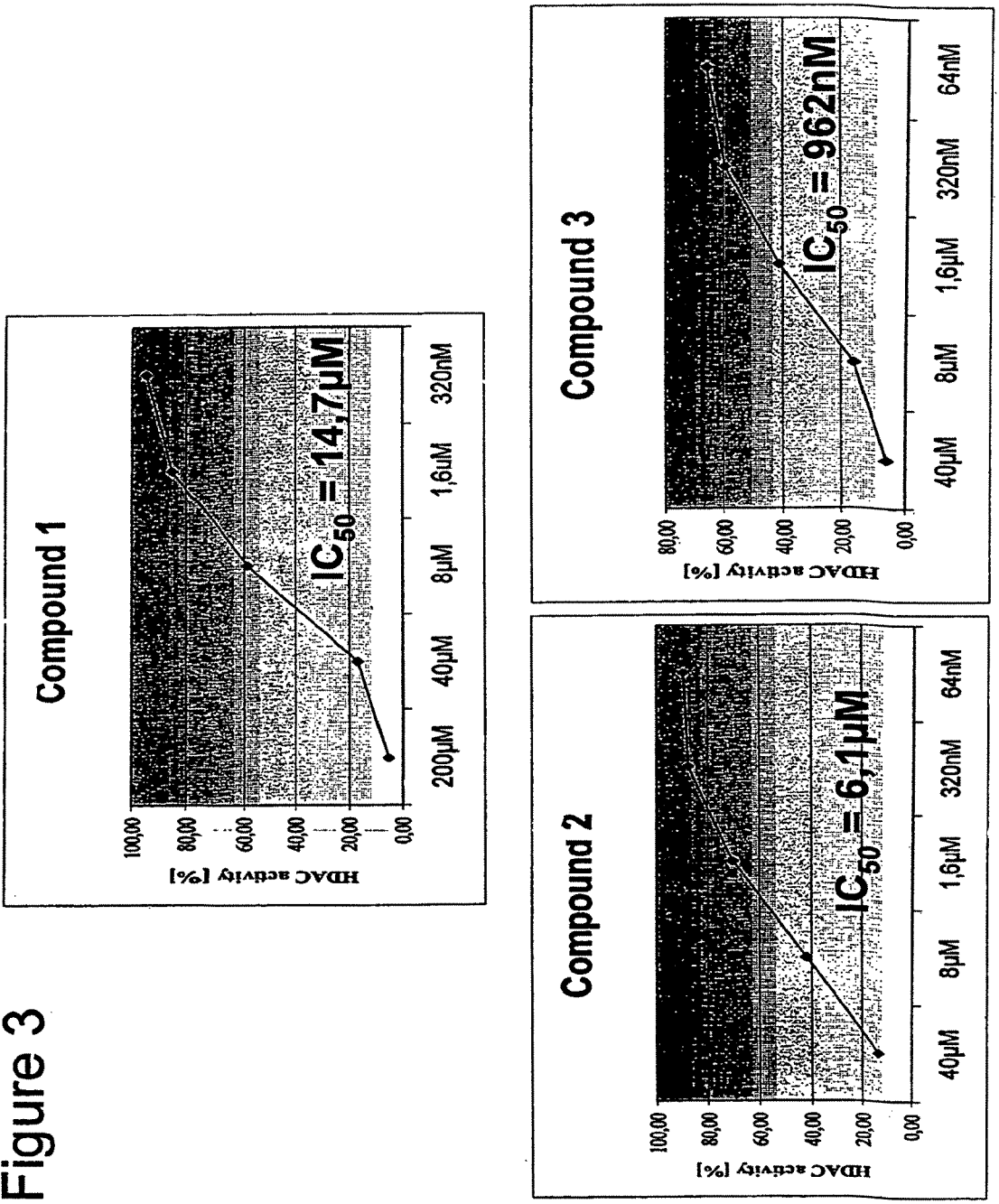
FIG. 3 shows the inhibition of in-vitro HDAC activity in nuclear extracts from HeLa cells after treatment with Compounds 1, 2 and 3 at the indicated concentrations. Relative HDAC activity is shown as percent of activity of untreated nuclear extracts.
Figure 4:
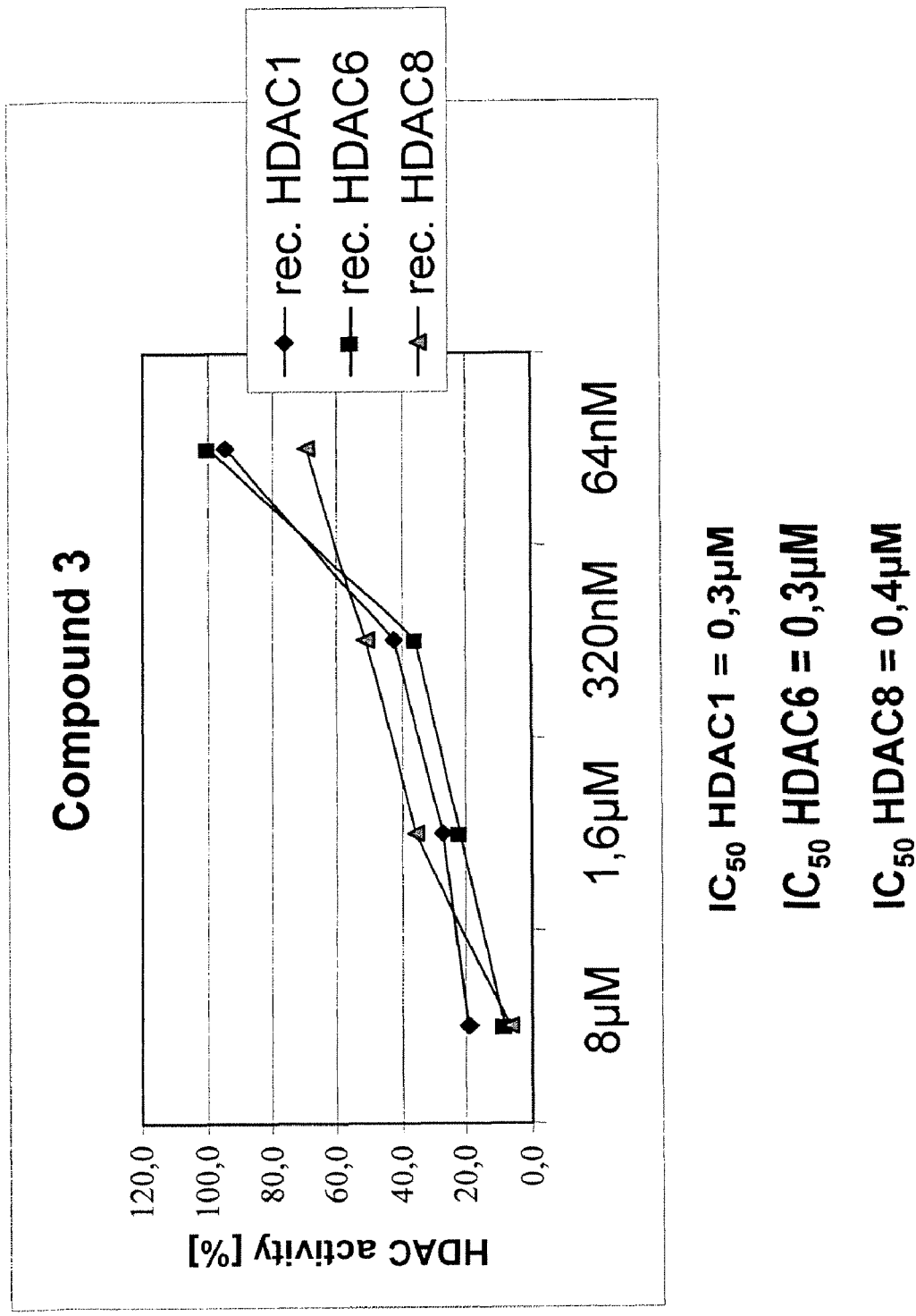
FIG. 4 shows the inhibition of in-vitro HDAC activity of recombinant HDAC1, HDAC6, and HDAC8 enzymes after treatment with Compound 3 at the indicated concentrations. Relative HDAC activity is shown as percent of activity of untreated HDAC enzymes.

Synthesis of Compound 1
(3-Cyclopentyl-N-hydroxy-propionamide)

To a solution of 3-Cyclopentyl-propionyl chloride (11.0 mL, 11.6 g, 72.0 mmol) in dichloromethane (50 mL) hydroxylamine hydrochloride (5.00 g, 72.0 mmol) and sodium bicarbonate (12.0 g, 144 mmol) were added. After stirring for 24 h at room temp. the reaction was quenched by addition of saturated ammonium chloride solution (50 mL). The layers were separated. The water layer was extracted with ethyl acetate (4×50 mL). The solvent of the combined organic layers was removed in vacuo. Precipitation of the crude product out of ethyl acetate by adding petroleum ether yielded the hydroxamate (5.25 g, 33.4 mmol, 46%) as a white solid. $^1$H NMR (300 MHz, [$D_6$-DMSO]: δ=0.74-0.91 (m, 2H), 1.05-1.25 (m, 4H), 1.36 (q, J=7.4 Hz, 4H), 1.54-1.71 (m, 5H), 1.94 (t, J=7.6 Hz, 2H), 8.59 (s, 1H) and 10.28 (s, 1H) (NH and OH). $^{13}$C NMR (75 MHz, [$D_6$-DMSO]: δ=25.6, 26.0, 29.7, 32.4, 36.5, 169.2 (C(=O)NHOH). MS: m/z calcd for ($C_8H_{14}NO_2$) [M+H]$^+$ 158; found 158.

Example 2

Synthesis of Compound 2
(3-Cyclohexyl-N-hydroxy-propionamide)

To a solution of 3-Cyclohexyl-propionyl chloride (12.1 mL, 12.6 g, 72.0 mmol) in dichloromethane (50-mL) hydroxylamine hydrochloride (5.00 g, 72.0 mmol) and sodium bicarbonate (12.0 g, 144 mmol) were added. After stirring for 24 h at room temperature the reaction was quenched by addition of saturated ammonium chloride solution (50 mL). The layers were separated. The water layer was extracted with ethyl acetate (4×50 mL). The solvent of the combined organic layers was removed in vacuo. Precipitation of the crude product out of ethyl acetate by adding petroleum ether yielded the hydroxamate (7.21 g, 42 mmol, 58%) as a white solid. $^1$H-NMR (300 MHz, [$D_6$-DMSO]: δ=0.95-1.12

(m, 2H), 1.38-1.69 (m, 6H), 1.62-1.77 (m, 3H), 1.94 (t, J=7.6 Hz, 2H), 8.58 (s, 1H) and 10.28 (s, 1H) (NH and OH); $^{13}$C-NMR (75 MHz, [D$_6$-DMSO]: δ=25.0, 31.8, 32.0, 32.3, 39.5, 169.5 (C(=)NHOH); MS: m/z calc. for (C$_9$H$_{17}$NO$_2$) [M+H]$^+$ 172; found 172.

Example 3

Synthesis of Compound 3
(3-Cyclohexyl-N-hydroxy-acrylamide)

3-Cyclohexyl-acrylic acid ethyl ester: to a cooled solution of oxalyl chloride (11.1 μL, 105 mmol) in dichloromethane (250 mL) was added at −78° C. a solution of dimethylsulfoxide (14.6 mL, 206 mmol) in dichloromethane (250 mL). After 5 min at the same temperature cyclohexylmethanol (10.8 mL, 87.5 mmol) and after additional 5 min triethylamine (60.7 mL, 438 mmol) were added. The reaction remained at −78° C. for two hours and then let warm to room temperature. The solvent was removed in vacuo. The resulting aldehyde was used for the next step without further purification. The crude cyclohexanecarbaldehyde was dissolved in toluene (200 mL) and ethanol (150 mL). After 15 min of stirring at 70° C. carbethoxy-methylene triphenylphosphorane (33.6 g, 96.5 mmol) was added in one portion. Stirring was continued for additional 24 hours. The solvent was removed in vacuo. The product was obtained by flash chromatography in 78% yield (12.5 g). $^1$H NMR (300 MHz, [D$_6$-DMSO]: δ=1.07-1.34 (m, 8H, CH$_3$ and cyclohexyl-CH$_2$), 1.60-1.80 (m, 5H, cyclohexyl-CH$_2$), 2.04-2.18 (m, 1H, cyclohexyl-CH); 4.16 (q, J=7.1 Hz, 2H, EtCH$_2$), 5.74 (dd, J=15.8 Hz and J=1.5 Hz, 1H, C=C—H), 6.89 (dd, J=15.8 Hz and J=6.8 Hz, 1H, C=C—H).

3-Cyclohexyl-acrylic acid: to a solution of 3-Cyclohexyl-acrylic acid ethyl ester (7.00 g, 38.4 mmol) in dioxane (200 mL) was added lithium hydroxide (4.03 g, 96.1 mmol) dissolved-in-water (70 mL). Because LiOH fell out methanol (170 mL) was added to the reaction. After 4 hours at 70° C. ¾ of the solvent was removed in vacuo. 2 N HCl was added until the pH reached 3. The mixture was treated with ammonium chloride (150 mL) saturated solution. The product was extracted with dichloromethane (200 mL×3). The combined organic phases were washed with saturated sodium solution (50 mL) and dried with magnesium sulfate. After filtration the solvent was removed in vacuo. The liquid was left at room temperature for 48 hours for crystallization to occur. The colourless crystalline product (2.01 g, 13.1 mmol) was obtained in 34% yield. $^1$H NMR (300 MHz, [D$_6$-DMSO]: δ=1.01-1.37 (m, 5H, cyclohexyl-CH$_2$), 1.55-1.79 (m, 5H, cyclohexyl-CH$_2$), 2.06-2.21 (m, 1H, cyclohexyl-CH); 5.69 (dd, J=15.7 Hz and J=1.5 Hz, 1H, C=C—H), 6.76 (dd, J=15.7 Hz and J=6.8 Hz, 1H, C=C—H), 12.01 (broad s, 1H, OH). $^{13}$C NMR (75 MHz, [D$_6$-DMSO]: δ=25.1, 25.4, 31.1 (cyclohexyl-CH$_2$), 39.4 (cyclohexyl-CH), 119.5 and 153.4 (C=C) 167.3 (COOH). MS: m/z calcd for (C$_9$H$_{14}$O$_2$) [M+H]$^+$ 155; found 155.

3-Cyclohexyl-N-hydroxy-acrylamide (K1 00003283): to a solution of 3-Cyclohexylacrylic acid (5.30 g, 31.3 mmol) in DMF (100 mL) was added EDC (1-(3-Dimethylaminopropyl)-3-ethylcarbodiimide hydrochloride) (7.80 g, 40.7 mmol) and HOBt (1-hydroxybenzotriazole hydrate) (5.07 g, 37.6 mmol). After stirring for 30 min at room temperature hydroxylamine hydrochloride (3.26 g, 47.0 mmol) and triethylamine (6.94 mL, 50.1 mmol) were added. After additional 18 hours stirring at room temperature the precipitate was filtered and washed with DMF. The DMF phases were combined. The solvent was concentrated in vacuo. 1 N HCl (50 mL) was added. After extraction with ethyl acetate (3×100 mL) and dichloromethane (2×100 mL) the organic layers were combined, washed with 1 N HCl (10 mL) and sodium chloride saturated solution (10 mL) and dried with magnesium sulfate. The solvent was removed in vacuo. The product was crystallized from ethyl acetate by addition of petroleum ether. This step removed large amounts of HOBt, the substance was then further purified by preparative HPLC using an acetonitrile/water gradient. This yielded (1.54 g, 9.08 mmol) of 3-Cyclohexyl-N-hydroxy-acrylamide. $^1$H NMR (300 MHz, [D$_6$-DMSO]: δ=0.99-1.35 (m, 5H) and 1.56-1.73 (m, 5H) (cyclohexyl-CH$_2$), 2.00-2.13 (m, 1H, cyclohexyl CH), 5.67 (d, J=15.7 Hz, 1H, C=C—H), 6.58 (dd, J=15.7 and J=6.3 Hz, 1H, C=C—H), 8.77 (s, 1H) and 10.49 (s, 1H) (NH and OH). $^{13}$C NMR (75 MHz, [D$_6$-DMSO]: δ=25.2, 25.5, 31.5 (cyclohexyl-CH$_2$), 41.1Acyclohexyl-CH), 118.8 and 147.1 (C=C), 162.8 (C(=O)NHOH). MS: m/z calcd for (C$_9$H$_{15}$NO$_2$) [M+H]$^+$ 170; found 170.

Example 4

Compounds 1, 2 and 3 inhibit HDAC activity, induce histone H4 hyperacetylation, and relieve transcriptional repression in a reporter cell line (FIG. 1 to 4). Histone hyperacetylation correlates with an open, de-condensed chromatin structure and gene activation, while hypoacetylation correlates with chromatin condensation and transcriptional repression. Acetylation is mediated by a series of enzymes with histone acetyltransferase (HAT) activity. Conversely, acetyl groups are removed by specific histone deacetylase (HDAC) enzymes. Disruption of these mechanisms gives rise to transcriptional misregulation. Transcription factors such as thyroid hormone receptor, PPARδ, retinoic acid receptor, N-CoR and AML/ETO recruit HDAC enzymes and thereby repress transcription when bound to a specific promoter region. This latter effect can be reenacted with a constitutive promoter containing UAS elements which recruits fusion proteins containing the heterologous DNA-binding domain of the yeast Gal4 protein fused to one of the above mentioned transcription factors. In the absence of the Gal4-fusion protein the reporter gene has a high basal transcriptional activity due to the presence of binding sites for other transcription factors in the thymidine kinase promoter.

Methods

Transcriptional reporter gene assay. The transcriptional assay for repressor activity exploits activation and derepression of a Gal4-dependent reporter gene (Hildebrand et al., 2001, J Biol Chem 276, 9889-95; Maurer et al., 2002, Blood 99, 2647-52). This assay is performed with specifically constructed permanent cell lines. 293T cell were stably transfected with a UAS TK luciferase reporter plasmid (Heinzel et al., 1997 Nature 387, pp 43-48) and an expression plasmid for the Gal4 DNA binding domain fused to an HDAC-dependent repressor molecule. While Gal4 fusion proteins repress this activity, HDAC inhibitors induce relief of this repression which can be detected as an increase in reporter gene activity (e.g. by luciferase activity detection assay).

Induction of histone hyperacetylation. These acetylated histones can be detected by Western Blot analysis of whole cell extracts from histone deacetylase inhibitor-treated 293T cells using antibodies specific for the acetylated N-terminal lysine residues of histones H4 (Göttlicher et al., 2001, EMBO J. 20, 6969-78).

In vitro inhibition of recombinant HDAC's. The determination of histone deacetylase activity in HeLa nuclear extracts or recombinant HDAC proteins from High5 insect cells is based on the specific deacetylation of an artificial substrate (Fluor de Lys, Biomol). The substrate turn over may be detected and quantified by fluorometry. By addition of a potential HDAC inhibitor the hydrolysis of the substrate is constrained resulting in a decreased fluorometric signal. $IC_{50}$ values may be calculated from dose-response curves.

The assay is separated in two steps: in the first step the substrate (Fluor de Lys/Biomol KI-104) is hydrolysed by histone deacetylases. In step two HDAC activity is terminated and the fluorophore is activated by the addition of a developer (Developer/Biomol KI-105). Nuclear extracts from HeLa cells (Biomol KI-140) or recombinant proteins and the potential HDAC inhibitor are mixed with reaction buffer (Biomol KI143) to a total volume of 25 µl per well of a 96 well plate. 25 µl substrate (1:100 dilution in reaction buffer) per well are added to start the reaction. A negative control without histone deacetylase activity and a positive control without HDAC inhibitor are treated likewise. The reaction is stopped after 15-60 min. by adding 50 µl developer (1:20 dilution in reaction buffer). After another 15 min. incubation time at room temperature the fluorescence signal is stable for 60 min and may be detected by a fluorescence reader (excitation filter: 390 nm, emission filter: 460 nm).

Results

As can be seen in FIG. 1, the Gal4 fusion protein represses the baseline activity of the TK promoter and the subsequent luciferase expression. Addition of Compounds 1, 2 and 3 relieve this repression as measured by increased expression and activity of luciferase in lysates of treated cells after 24 hours. Both, Compound 1 and 2 induce luciferase reporter gene expression after stimulation of cells for 24 hours starting at a concentration of 8 µM (2-3 fold) with a maximum induction of more than 20 fold at 200 µM. Compound 3, however, induces expression of reporter gene already at a concentration of 1.6 µM with a maximum induction of almost 40 fold at 40 µM.

Since histone deacetylase inhibitors shift the enzymatic balance between histone acetyl transferases (HAT's) and histone deacetylases (HDAC's) towards HAT's by blocking HDAC's, they induce the accumulation of N-terminally hyperacetylated histones H4. This can be seen in FIG. 2 by the induction of histone hyperacetylation after treatment of 293T cells for 6 hours with Compounds 1, 2 and 3. Hyperacetylation can be seen with Compounds 1 and 2 at a concentration as low as 1.6 µM with a maximum induction at 40 µL, whereas compound 3 induces hyperacetylation starting at 320 nM.

Since most HDAC's reside in the nucleus, highest HDAC activity can be measured in nuclear extracts. As demonstrated in FIG. 3, HDAC activity in nuclear extracts is dramatically reduced in the presence of Compounds 1, 2 and 3, with a 50% reduction of HDAC activity at a concentration of 14.7 µM for Compound 1, at 6.1 µM for Compound 2, and at 0.9 µM for Compound 3.

Results obtained with Compound 3 in nuclear extracts could be confirmed with recombinant HDAC's. As demonstrated in FIG. 4, HDAC activity of recombinant HDAC1, HDAC6, and HDAC8 is dramatically reduced in the presence of Compound 1 and 2, with a 50% reduction of HDAC activity at a concentration of 0.3 to 0.4 µM for Compound 3.

Example 5

Induction of growth arrest, apoptosis and down-regulation of $BCL-X_L$ after treatment of cancer cells with Compounds 1, 2 and 3. The treatment of tumor cell lines with histone deacetylase inhibitors leads to histone hyperacetylation and the transcriptional regulation of target genes. Although the discrete mechanism of action varies, cancer therapy still depends on an ability to engender apoptosis in cancer cells as a final common pathway. HDAC inhibitors have already been shown to induce apoptosis in certain cancer cells through down-regulation of the anti-apoptotic molecules, such as $BCL-X_L$ and BCL-2. Anti-apoptotic BCL2 family members seem to be involved in resistance of tumors to apoptosis. For example, high expression of $BCL-X_L$ is found in many human cancers and is often a negative prognostic factor. Accordingly, downregulation of $BCL-X_L$ expression in certain cancer cells either induces apoptosis directly or sensitizes cells to apoptotic stimuli.

In general, induction of apoptosis can be exploited therapeutically using HDAC inhibitors in cancer therapy.

Methods

Protein expression profiling. The expression pattern induced by histone deacetylase inhibitors can be monitored by Western Blot analysis with antibodies against p21 and $BCL-X_L$ using whole cell extracts of cells treated with the respective compounds at the indicated concentrations. Modulation of protein expression is exemplified by the induction of expression of the cell cycle inhibitor/tumor suppressor p21 and the suppression of expression of the anti-apoptotic molecule BCL-XL.

Growth inhibition of tumor cell lines. The reduction in cellular biomass was measured by SRB-assay. For this assay cells were seeded in 96 well culture dishes at densities between 3000 and 8000 cells per well. After recovery of 24 hours cells were cultured for 48-72 hours in the absence or presence of the indicated concentrations of compounds. Synergistic reduction in total cellular biomass was assayed through SRB-assay by adding the compounds in the medium at the indicated concentrations and cultivate the cells for further 48 hours.

Cells were fixed with cold Trichloracetat (TCA) producing a final TCA concentration of 10%. After 1 hour of incubation at 4° C. the cells were washed five times with water and air dried. Fixed cells were stained for 30 minutes with 0.4% (wt/vol) Sulforhodamine B (SRB) dissolved in 1% acetic acid and washed four times with 1% acetic acid to remove unbound dye. After air drying bound dye was solubilized with 10 mM unbuffered Tris base (pH 10.5) for 5 minutes. Optical densities (OD) were read on a Molecular Devices Versa Max tunable microplate reader at 520-550 nm. Four test wells for each dose-response were set in parallel with 12 control wells per cell line. Measurement of the cell population density at time 0 (To; the time at which the drug was added) was also made from 12 reference wells of cells fixed with TCA just prior to drug addition to the test plates. Background OD of complete medium with 5% FBS fixed and stained as described above was also determined in 12 separate wells. From the unprocessed OD data from each microtiter plate the background OD measurements (i.e. OD of complete medium plus stain and OD of cells at $T_0$) were subtracted thus giving the reduction of cellular biomass of the cells.

Measurement of Apoptosis. FACS analysis of the cell cycle by propidium iodide (PI) staining. The cell cycle can be divided into four different sections: During $G_{0/1}$-phase cells are in senescence or proliferate, in S-phase cells start replicating their DNA, and during G2- and M-phase cells undergo mitosis. The cellular DNA content correlates with cell cycle progression: while cells in $G_{0/1}$ phase possess one set of chromosomes, cells in G2-. and M-phase possess two full sets of chromosomes. Cells in S-phase are still replicating their DNA and therefore exhibit a DNA content between one and two sets of chromosomes. Degradation of DNA is a marker for apoptosis. The sub-G1 area indicates the hypodiploid DNA peak corresponding to cells with fragmented DNA undergoing apoptosis Using a dye that intercalates with DNA (such as propidium iodide—PI) the cellular DNA content was determined. Between $5 \times 10^5$-$1 \times 10^6$ cells were seeded out in cell culture dishes and treated for the desired time with the desired amount of test compound. After the incubation cells were harvested, washed in cold PBS, and the cell pellet was resuspended in 1 ml 70% ethanol (−20° C.). These cell pellets may be shelved for several month.

For PI staining 3 ml cold sodium citrate solution (38 mM, pH 7.4) was added, cells were pelleted and stained with 500 μl sodium citrate solution (38 mM, pH 7.4) containing 50 μg/ml PI and 5 μg/ml RNase. After a 30 minute incubation time at 37° C. in darkness, cells were analyzed via FACS analysis. The sub-$G_1$-peak constitutes the amount of apoptotic cells.

Results

Figure 5:
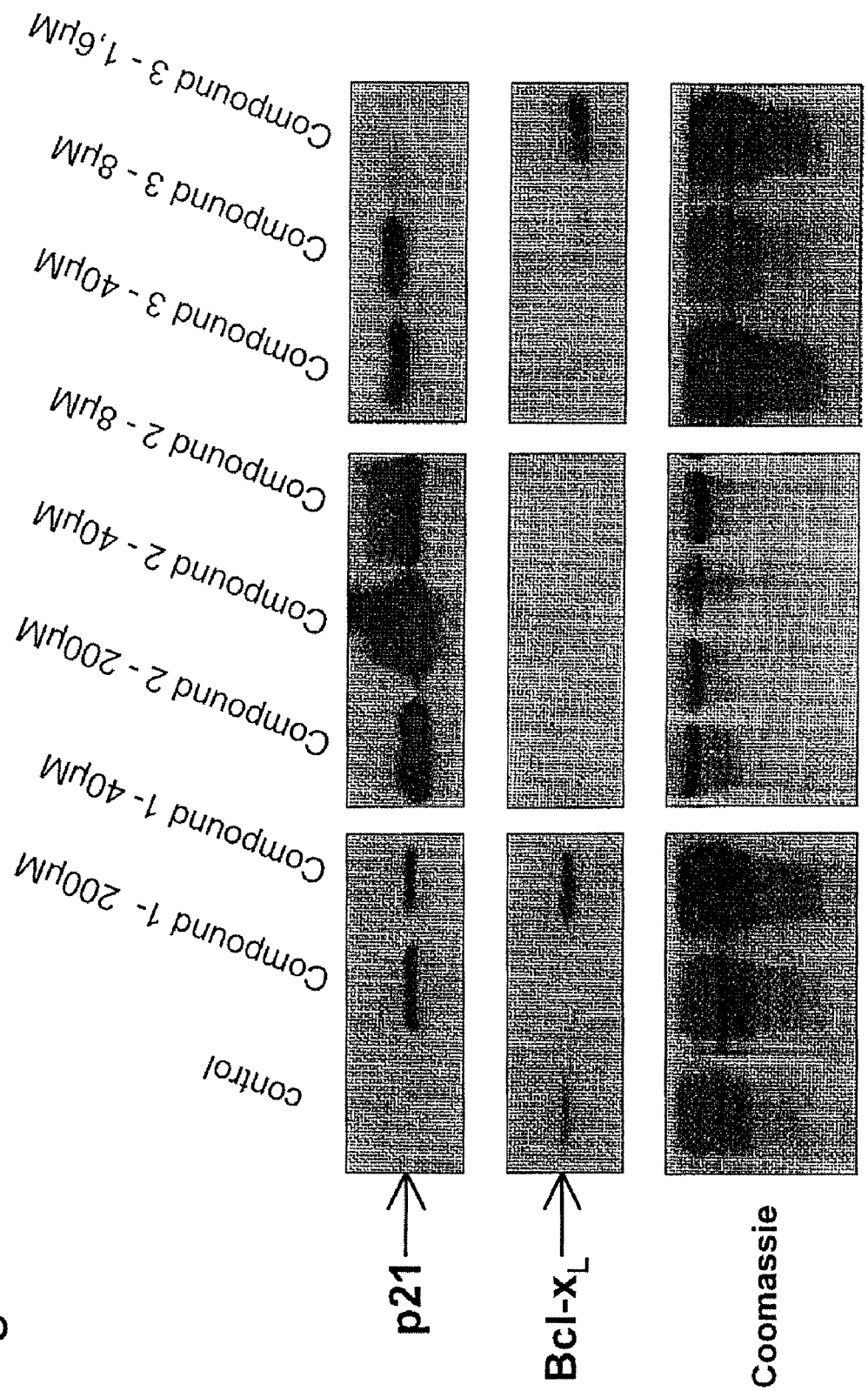
FIG. 5 shows on the protein level the down-regulation of the anti-apoptotic molecule BCL-XL and up-regulation of the cell cycle inhibitor p21 in K562 cells induced after treatment with Compounds 1, 2 and 3 for 36 hours at the indicated concentrations.

The expression of the growth arrest signaling tumor suppressor protein p21 (p21/waf) and the anti-apoptotic protein BCL-$X_L$ was analyzed upon treatment with Compounds 1, 2 and 3. A down-regulation of the latter is regarded as one important pre-requisite for the induction of apoptosis. FIG. 5 shows that Compounds 1, 2 and 3 in fact induces increased protein expression levels of p21 and at the same time down-regulates BCL-$X_L$ protein levels. Both, Compound 2 and 3 induce p21 expression and BCL-XL downregulation at 8 μM, whereas Compound 1 induces p21 expression at 40 μM and BCL-XL downregulation at 200 μM.

Growth of various human tumor cell lines of breast, colon, pancreas and prostate origin were inhibited by Compounds 1, 2, and 3 (FIG. 6). The concentrations inducing 50% growth arrest ranged from 8 to 70 μM (mean 33 μM) for Compound 1, from 5 to 26 μM (mean 15 μM) for Compound 2, and from 0.5 to 8 μM (mean 2.6 μM) for Compound 3.

Figure 7:
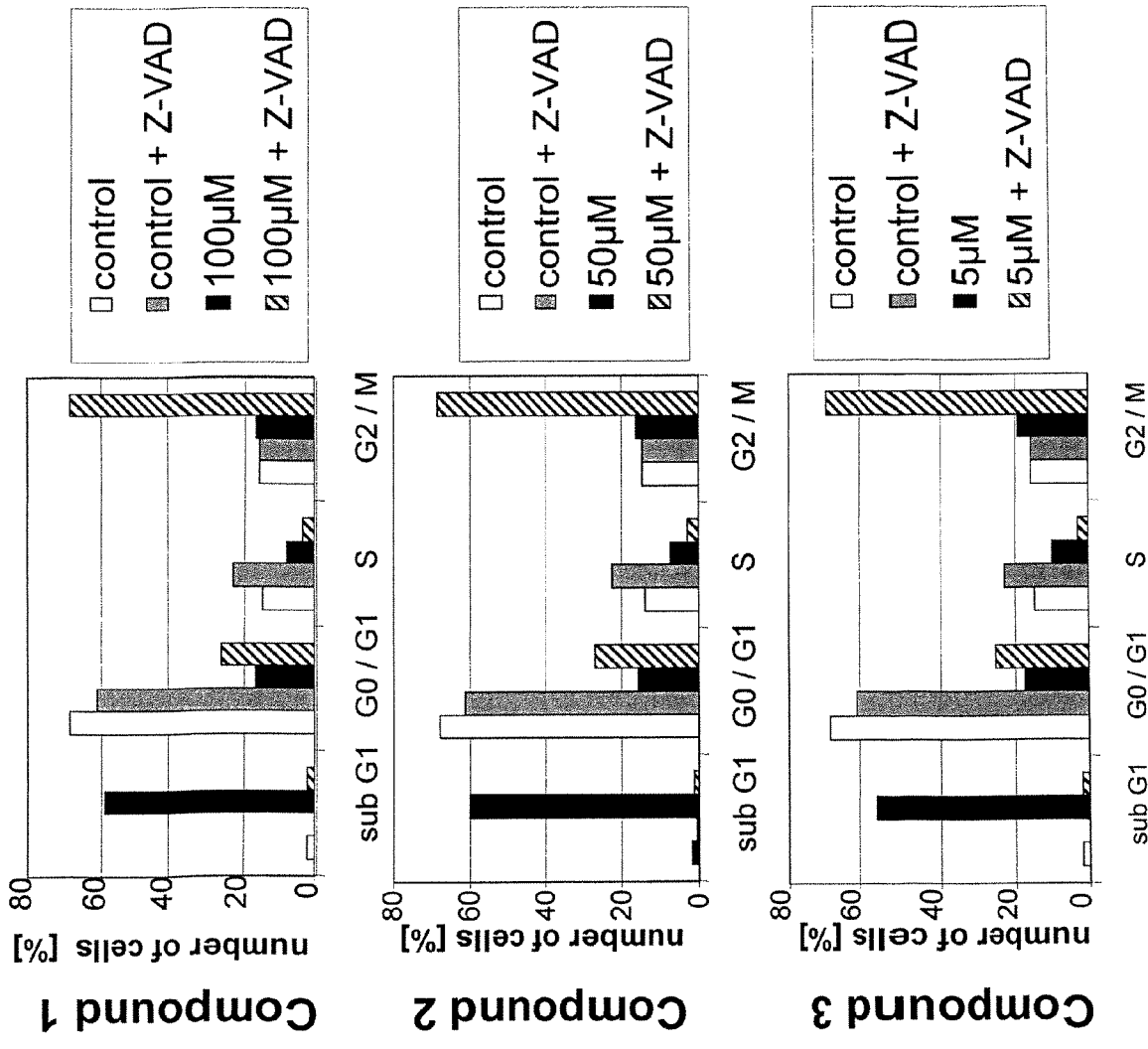
FIG. 7 shows the induction of apoptosis in BV-173 cells after treatment for 24 hours with Compounds 1, 2 and 3 at the indicated concentrations. Apoptosis is demonstrated by the increase of a sub-G1 population in Propidium Iodine treated cells, which is reduced to baseline levels after treatment with a pan-caspase inhibitor Z-VAD.

Studies using the BV-173 cell line consolidated the activity of Compound 1 and 2 as inducers of programmed cell death (apoptosis). Examples of this type of analysis are presented in FIG. 7. The "sub-G1 area (M1) indicates the hypodiploid DNA peak corresponding to cells with fragmented DNA undergoing apoptosis, which is dramatically increased to 50-60% in cells treated with Compound 1 at 100 μM, Compound 2 at 50 μM and Compound 3 at 5 μM. This apoptotic process is however completely blocked in the presence of a pan-caspase inhibitor, Z-VAD, which again confirms the induction of apoptosis by Compounds 1, 2, and 3.

What is claimed is:

1. A method of treating an inflammatory disorder, diabetes, or cirrhosis in a subject in need thereof, comprising administering to said subject an effective amount of a compound of formula (I):

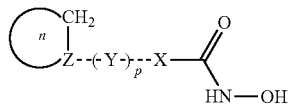

or a pharmaceutically acceptable salt or a physiologically functional derivative thereof wherein:
the ring n including Z is selected from the group consisting of cyclopentyl and cyclohexyl;
X is $CH_2$ or, if the dotted line at X represents a double bond, X is CH,
Y is selected from the group consisting of CH, $CH_2$, $CH_2$—$CH_2$;
p is 0 or 1;
wherein the physiologically functional derivative is selected from the group consisting of ethers, esters, N-alkylated or acetylated hydroxamic acids, 2,5-dihydro-[1,2,4]oxodiazolyl or 4,5-dihydro-[1,2,4]-oxadiazolyls of the compound of formula (I); and
with the proviso that the following compounds are excluded:

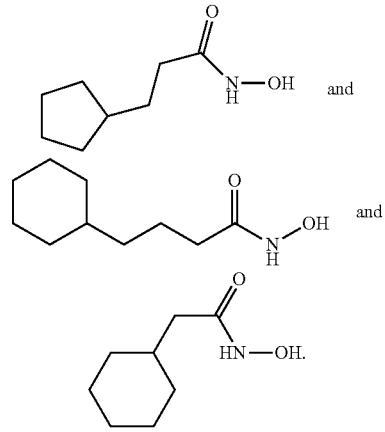

2. A method of treating an inflammatory disorder, diabetes or cirrhosis in a subject in need thereof, comprising:
administering an effective amount of a pharmaceutical composition to a subject in need thereof, thereby inhibiting abnormal gene expression characteristic of inflammatory disorders, diabetes, or cirrhosis, the pharmaceutical composition comprising a compound as defined in claim 1 in free from or in the form of a pharmaceutically acceptable salt or a physiologically acceptable derivative thereof, and a pharmaceutically acceptable excipient.

3. A method according to claim 1, wherein the compound is 3 Cyclohexyl-N-hydroxy-propionamide.

4. A method according to claim 1, wherein the compound is 3-Cyclohexyl-N-hydroxy-acrylamide.

5. A method of treating an inflammatory disorder, diabetes, or cirrhosis in a subject in need thereof, comprising administering to said subject an effective amount of 3-Cyclopentyl-N-hydroxy-propionamide.

* * * * *